US00PP27015P2

(12) United States Plant Patent
van Noort

(10) Patent No.: US PP27,015 P2
(45) Date of Patent: Aug. 2, 2016

(54) ***ECHINACEA* PLANT NAMED 'MEDITATION WHITE'**

(50) Latin Name: ***Echinacea* hybrid**
Varietal Denomination: Meditation White

(71) Applicant: Marco van Noort, Warmond (NL)

(72) Inventor: Marco van Noort, Warmond (NL)

(73) Assignee: MARCO VAN NOORT BREEDING BV, Warmond (NL)

( * ) Notice: Subject to any disclaimer, the term of this patent is extended or adjusted under 35 U.S.C. 154(b) by 280 days.

(21) Appl. No.: 13/999,144

(22) Filed: Jan. 17, 2014

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

Bransford Webbs Plant Company, retrieved on Dec. 14, 2015, retrieved from the Internet at <http://www.bransford.co.uk/plant_profiles_echinacea_white_meditation.html> 2 pp.*

Royal Horticultural Society *Echinacea* White Meditation, retrieved on Dec. 14, 2015, retrieved from the Internet at <https://www.rhs.org.uk/Plants/334780/Echinacea-White-Meditation/Details> 2 pp.*

* cited by examiner

*Primary Examiner* — June Hwu
(74) *Attorney, Agent, or Firm* — Penny J. Aguirre

(57) ABSTRACT

A new cultivar of hybrid *Echinacea* named 'Meditation White' characterized by its healthy, dense, and compact plant habit, its inflorescences with ray florets that are white in color, its flowering at a young age requiring only 4.5 months to develop into a branched flowering plant from tissue culture, and its floriferous flowering habit.

2 Drawing Sheets

Botanical classification: *Echinacea* hybrid.
Variety denomination: 'Meditation White'.

BACKGROUND OF THE INVENTION

The present invention relates to a new and distinct cultivar of *Echinacea* of hybrid origin and will be referred to hereafter by its cultivar name 'Meditation White'. 'Meditation White' is an herbaceous perennial grown for landscape and container use.

The new invention arose from an ongoing controlled breeding program in Warmond, The Netherlands. The objective of the breeding program is to develop cultivars of *Echinacea* with superior health and rich-flowering habits.

The Inventor made a controlled cross in July 2008 in his test garden in Warmond, The Netherlands between *Echinacea purpurea* 'Alba' (not patented) as the female parent, and *Echinacea* 'Meditation' (U.S. Plant Pat. No. 25,602), as the male parent. 'Meditation White' was selected in July 2010 as a single unique plant amongst the resulting seedlings from the above cross.

Asexual propagation of the new cultivar was first accomplished by division in Warmond, The Netherlands in January 2011 by the Inventor. Asexual propagation by tissue culture using meristem tissue and division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Meditation White' as unique cultivar of *Echinacea*.

1. 'Meditation White' exhibits a healthy, dense, and compact plant habit.
2. 'Meditation White' exhibits inflorescences with ray florets that are white in color.
3. 'Meditation White' exhibits flowering at a young age; requiring only 4.5 months to develop into a branched flowering plant from tissue culture.
4. 'Meditation White' exhibits a floriferous flowering habit.

The female parent of 'Meditation White', 'Alba', differs from 'Meditation White' in having a less compact plant habit, in being much less densely branched, and in flowering at an older age post propagation. The male parent of 'Meditation White', 'Meditation', differs from 'Meditation White' in having flowers that are red-purple in color. 'Meditation White' can be most closely compared to the *Echinacea* cultivars 'Happy Star' (not patented) and 'White Swan' (not patented). Both 'Happy Star' and 'White Swan' are similar to 'Meditation White' in having inflorescences with single ray florets that are white in color. 'Happy Star' differs from 'Meditation White' in having a less compact plant habit, in being less densely branched, and in being less floriferous. 'White Swan' differs from 'Meditation White' in having a less compact plant habit, in being less densely branched, in being less floriferous, and in having flowers that are larger in size.

BRIEF DESCRIPTION OF THE DRAWINGS

The accompanying colored photographs illustrate the overall appearance and distinct characteristics of the new *Echinacea*. The photographs were taken of six month-old plants of the new cultivar as field grown in Warmond, The Netherlands (placed in a container for the photographs).

The photograph in FIG. 1 illustrates the overall habit and appearance of 'Meditation White'.

Figure 1:
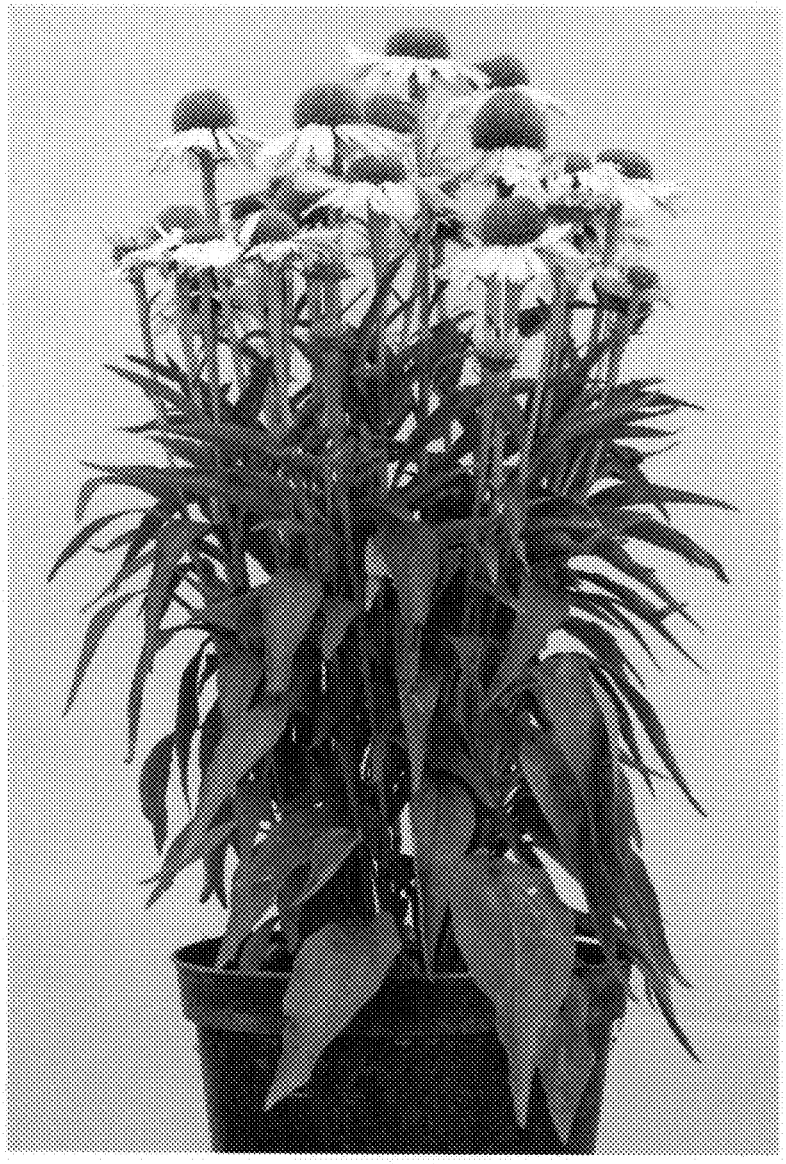
Figure 2:
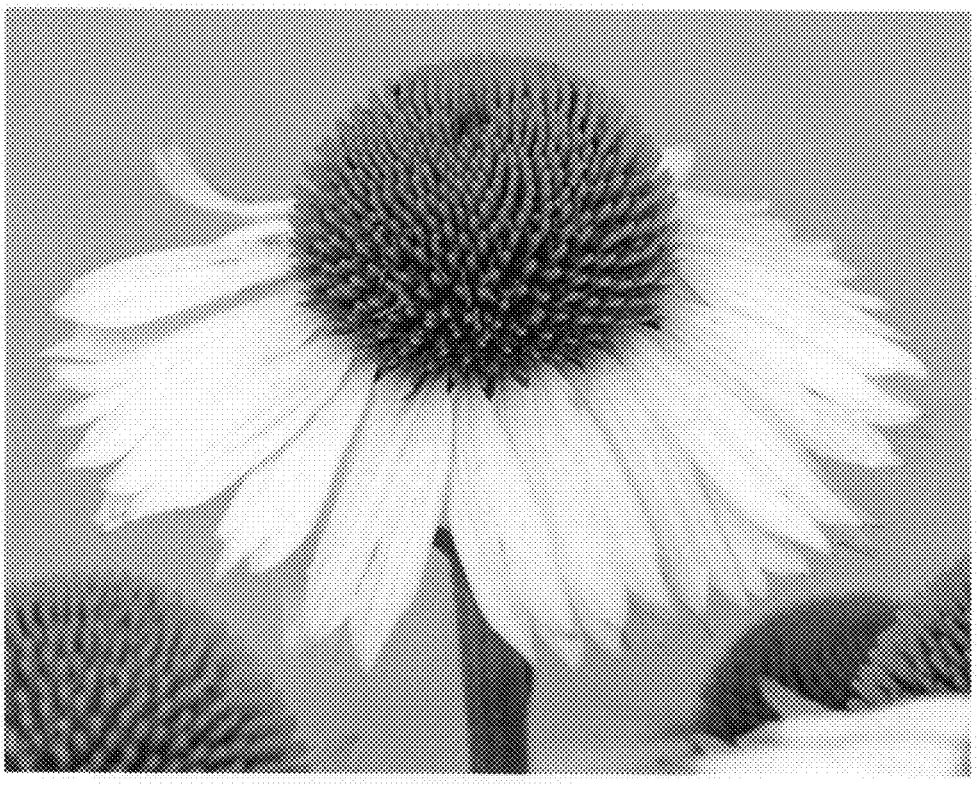

The photograph in FIG. 2 provides a close-up view of an inflorescence of 'Meditation White'.

Figure 3:
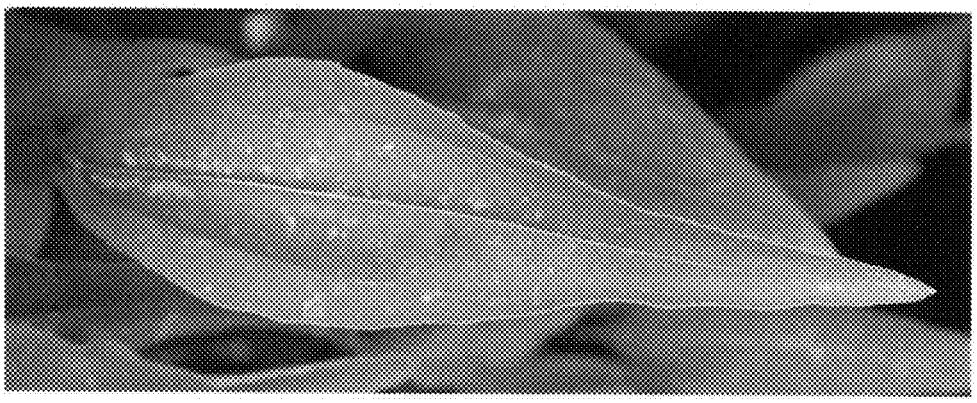

The photograph in FIG. 3 provides a close-up view of a leaf of 'Meditation White'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of six month-old plants of the new cultivar as field grown in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from early July to late September, in Warmond, The Netherlands.

*Plant type.*—Herbaceous perennial.

*Plant habit.*—Compact, upright, and densely-branched.

*Height and spread.*—An average of 50 cm in height and 45 cm in width.

*Cold hardiness.*—At least in U.S.D.A Zone 3.

*Diseases resistance.*—Similar susceptibility and resistance to diseases and pests as other *Echinacea* varieties.

*Root description.*—Fibrous and fine.

*Propagation.*—Tissue culture using meristem tissue and division.

*Growth rate.*—Moderate.

Stem description:

*Shape.*—Rounded.

*Stem color.*—144B to 144C.

*Stem size.*—An average of 6 mm in diameter and 28.3 cm in length (from base of plant to base of uppermost leaf).

*Stem strength.*—Strong.

*Stem aspect.*—Stems grow in an average angle of 85° from the base (0°=horizontal).

*Stem surface.*—Moderately rough to touch and densely covered with very short strigose hairs about 1.5 mm in length and NN155D in color.

*Stem number.*—Densely branched, an average of 10 main stems.

*Internode length.*—Average of 3 cm in length.

*Branching.*—Main flowering stem grows from base, dense.

Foliage description:

*Leaf shape.*—Narrow ovate.

*Leaf division.*—Simple.

*Leaf base.*—Attenuate.

*Leaf apex.*—Acute.

*Leaf venation.*—Pinnate, color: upper surface; 144B, lower surface; 144D.

*Leaf margins.*—Entire, slightly undulate.

*Leaf attachment.*—Petiolate.

*Leaf arrangement.*—Alternate.

*Leaf size.*—Average of 12.9 cm in length and 4.1 cm in width.

*Leaf color.*—Young upper surface; 143A, young lower surface; color between 143A and 144A, mature upper surface; 137B, mature lower surface; 137B.

*Leaf surface.*—Upper and lower surfaces are moderately glossy and densely covered with short strigose hairs an average of 1 mm in length and NN155D in color.

*Petioles.*—V-shaped, 5.5 cm in length and 3 mm in diameter, color upper surface 145B with margins 143A, color lower surface 145B, both surfaces glossy and covered with short strigose hairs, an average length is 0.5 mm and NN155D in color.

Flower description:

*Type.*—Terminal capitulum consisting of ray florets and disc florets.

*Capitulum number.*—An average of 3 per stem.

*Lastingness of inflorescence.*—About 2 weeks.

*Capitulum size.*—Matures to about 4.5 cm in height and 7.8 cm in diameter, disc diameter is an average of 3.3 cm and disc height is an average of 2.7 cm.

*Fragrance.*—Moderately faint, sweet fragrance.

*Involucral bracts or phyllary.*—About 60 arranged in 3 overlapping rows, average of 1.1 cm in length and 3 mm in width, surface appearance is dull, cuneate base, acute apex, entire margin, narrowly ovate to ovate in shape, color upper surface is 143B, with base is 144D, color lower surface 137A to 137B, upper surface is smooth, lower surface is very sparsely covered with very short hairs; an average of 0.2 mm in length and 157D in color, margins are moderately covered with very short hairs; an average of 0.4 mm in length and 157D in color.

*Buds.*—Flattened globular in shape, immature ray florets near vertical (upright), an average of 1.7 cm in length and 2.2 cm in diameter, color; 143A, immature ray florets are 150D with tips 145B.

*Peduncle.*—Strong, terminal is an average of 14.2 cm in length (from uppermost leaf to base of inflorescence) and 4 mm in diameter, fourth peduncle is an average of 13.1 cm in length and 4 mm in diameter (from uppermost leaf to base of inflorescence), terminals held upright with secondary peduncles held at an average angle of 15° to vertical, color 144C, surface is moderately covered with short strigose hairs about 0.7 mm in length and NN155D in color.

*Ray florets.*—Rotate, average of 28 per inflorescence, oblanceolate in shape, upper surface smooth and dull, lower surface smooth and moderately ribbed lengthways, about 3.6 cm in length and 8 mm in width, emarginate to cleft apex, cuneate base, entire margin, slightly drooping in an average angle of about 20° downward from horizontal, color of upper surface when opening; a color between 155A and 157D, tip is 150D, base is 145B, color of lower surface when opening; closest to 157D, tip and base is 145B, color of upper surface when fully open; closest to 150D, base is 145B, color of lower surface when fully open; 150D, tip and base is 145B.

*Disk flowers (bisexual).*—Numerous, about 400, arranged spirally on disc, apex is acute on upper 20% that is free, fused (tubular) base, entire margin, average of 9 mm in length and 2.5 mm in width, upper surface and lower surface are smooth and glossy, color when opening and fully open upper and lower surfaces; free tips are 144B, mid-section is 157D and transparent, base is 150C.

*Disk spines.*—Average of 400, acicular in shape, acute apex, attenuate base, smooth and glossy surface, color is 14B at apex, 144B in mid region and 145D at base.

*Receptacle.*—Triangular in shape, an average of 1.2 mm in height and 1.3 mm in diameter, and NN155A in color.

Reproductive organs (present on disk florets only):

*Gynoecium.*—Pistil; 1, 8 mm in length, style is about 6 mm in length and 150C in color, stigma is unequal decurrent and N144A in color, ovary is 145D in color.

*Androcoecium.*—Stamens; 4, filaments; 3 mm in length and 157D in color, anthers; linear in shape, about 3 mm in length and 200A in color, pollen is moderate in quantity and 14A in color.

*Fruit/seed.*—No seed production has been observed to date.

It is claimed:

1. A new and distinct cultivar of *Echinacea* plant named 'Meditation White' as herein illustrated and described.

* * * * *